(12) United States Patent
Duan et al.

(10) Patent No.: US 11,262,341 B2
(45) Date of Patent: Mar. 1, 2022

(54) METHOD FOR NON-DESTRUCTIVE DETECTION OF EGG FRESHNESS BASED ON CENTROID MEASUREMENT

(71) Applicant: Northwest Agriculture and Forestry University, Shaanxi (CN)

(72) Inventors: Xiang Duan, Shaanxi (CN); Wen Tan, Shaanxi (CN); Xuebo Liu, Shaanxi (CN); Ying Lan, Shaanxi (CN); Qinjun Zhang, Shaanxi (CN); Lu Yang, Shaanxi (CN)

(73) Assignee: Northwest Agriculture and Forestry University, Shaanxi (CN)

(*) Notice: Subject to any disclaimer, the term of this patent is extended or adjusted under 35 U.S.C. 154(b) by 0 days.

(21) Appl. No.: 17/267,008

(22) PCT Filed: Sep. 6, 2019

(86) PCT No.: PCT/CN2019/104660
§ 371 (c)(1),
(2) Date: Feb. 8, 2021

(87) PCT Pub. No.: WO2020/173072
PCT Pub. Date: Sep. 3, 2020

(65) Prior Publication Data
US 2021/0389292 A1  Dec. 16, 2021

(30) Foreign Application Priority Data
Feb. 27, 2019 (CN) .......................... 201910145645.7

(51) Int. Cl.
*G01N 33/08* (2006.01)
*G01M 1/12* (2006.01)

(52) U.S. Cl.
CPC ............ *G01N 33/08* (2013.01); *G01M 1/122* (2013.01)

(58) Field of Classification Search
CPC .............................. G01N 33/08; G01M 1/122
See application file for complete search history.

(56) References Cited

U.S. PATENT DOCUMENTS

| 7,389,676 B2 * | 6/2008 | Horst ...................... G01N 33/08 |
| 2021/0247318 A1 * | 8/2021 | Xie ......................... G01N 33/08 |

FOREIGN PATENT DOCUMENTS

| CN | 101718682 A | * | 6/2010 |
| CN | 102445456 A | * | 5/2012 |

(Continued)

OTHER PUBLICATIONS

Wei, Xiaobiao et al., "Test and Comprehensive Model for Non-destructive Detection of Egg Freshness", Transactions of Chinese Society of Agricultural Engineering, Mar. 2009, submit with English abstract, pp. 242-247.

(Continued)

*Primary Examiner* — Natalie Huls
(74) *Attorney, Agent, or Firm* — JCIP Global Inc.

(57) ABSTRACT

A method for non-destructive detection of egg freshness based on centroid measurement. A real-time distance between the centroid position of an egg and the top of a small end of the egg is measured, the ratio of the distance to the length of the egg is defined as a centroid ratio, models are respectively established regarding a centroid ratio change and the number of days the egg has been stored, and regarding the centroid ratio change and the egg freshness, and the number of the days the egg has been stored and the egg freshness are predicted by means of the established models.

7 Claims, 9 Drawing Sheets

(56) References Cited

FOREIGN PATENT DOCUMENTS

| CN | 102628723 A | * | 8/2012 |
|---|---|---|---|
| CN | 102628724 | | 8/2012 |
| CN | 106018487 | | 10/2016 |
| CN | 207636577 U | * | 7/2018 |
| CN | 108663367 | | 10/2018 |
| CN | 108802060 | | 11/2018 |
| CN | 109813494 | | 5/2019 |
| JP | 2006105646 | | 4/2006 |
| JP | 2006300810 | | 11/2006 |
| KR | 101829544 B1 | * | 2/2018 |

OTHER PUBLICATIONS

"International Search Report (Form PCT/ISA/210) of PCT/CN2019/104660," dated Dec. 9, 2019, with English translation thereof, pp. 1-6.

* cited by examiner

METHOD FOR NON-DESTRUCTIVE DETECTION OF EGG FRESHNESS BASED ON CENTROID MEASUREMENT

CROSS-REFERENCE TO RELATED APPLICATION

This application is a 371 of international application of PCT application serial no. PCT/CN2019/104660, filed on Sep. 6, 2019, which claims the priority benefit of China application no. 201910145645.7, filed on Feb. 27, 2019. The entirety of each of the above mentioned patent applications is hereby incorporated by reference herein and made a part of this specification.

BACKGROUND

Technical Field

The present invention relates to the technical field of agricultural and animal product detection, and particularly relates to a method for rapid and non-destructive detection of egg freshness based on centroid measurement.

Description of Related Art

Eggs, as an important source of protein nutrition for consumers, have the characteristics of rich nutrition, easy digestion and absorption and the like, and are deeply loved by the public. The per capita consumption of poultry eggs in China has ranked first in the world, and the egg consumption demand is still growing rapidly. At present, eggs are mostly processed and produced in a large-scale industrialized way, so the eggs are easy to deteriorate due to external influence in processing, storage and transportation links. At present, egg quality and freshness grading is mainly determined by manual or physical and chemical index measurement, this will cause low production efficiency, high cost, and damage to the eggs, and it is difficult to cope with freshness changes of the eggs in the storage process for rapid and low-cost detection. Therefore, inventing a method for rapid and non-destructive detection of egg freshness is of great significance on the improvement of egg production efficiency.

At present, there are many methods for egg freshness detection. However, they all have certain defects, such as measurement of Haugh index, pH, viscosity, and the like of eggs. The measurement of these indexes will cause damage to the eggs, the detection period is long, and the procedures are complicated. A machine vision technology can be used for egg freshness identification, but it will be influenced by the color and thickness of the eggshell and the brightness of a light source. An infrared spectroscopy technology can also be used for egg freshness detection, but the data analysis workload is very great, and it is easily influenced by external environment. Foreign countries use technologies such as a gas chromatography and gas chromatograph-mass spectrometer to detect volatile components of eggs, which can accurately reflect the volatile substance composition of the eggs in each period, but the disadvantages are that the cost is high, the detection period is long, and the technology is not suitable for large-scaled industrialized detection. Therefore, how to improve the detection technology, reduce the cost, increase the economic efficiency and solve the problem of egg freshness detection is of great significance.

The center of mass is called as centroid for short, and refers to that the mass of a substance is systematically regarded to be concentrated on an imaginary point which is a geometric center of a two-dimensional shape. The centroid position is of great significance in engineering. The deviation of the centroid position of an object will influence the whole motion state of the system. The present invention judges the egg freshness by measuring the centroid position of the egg in different periods and establishing a relationship with the Haugh index.

SUMMARY

Technical Problem

In view of the technical problems, an objective of the present invention is to find a method for rapid and non-destructive detection of egg freshness.

Technical Solution

A method for non-destructive detection of egg freshness based on centroid measurement includes the following steps:

data acquisition: accurately measuring the centroid position of an egg by a centroid measuring instrument, and obtaining the value of the egg centroid ratio by calculating the ratio of the distance from the centroid to the top of a small end of the egg to the length of the egg; and data processing: establishing mathematical models between the egg centroid ratio at different temperatures and different placing positions and the egg Haugh index, where according to the established models, the egg freshness is able to be directly represented according to the centroid ratio, and the objective of rapid, accurate and non-destructive detection of egg freshness is achieved.

Further, in step S2, fitted equations are respectively established between the egg centroid ratio at three different temperatures and the number of days the egg has been stored.

Further, in step S2, fitted equations are respectively established between the egg centroid ratio at three different placing positions and the number of days the egg has been stored.

Further, in step S2, fitted equations are respectively established between the egg centroid ratio at three different temperatures and the egg Haugh index.

Further, in step S2, fitted equations are respectively established between the egg centroid ratio at three different placing positions and the egg Haugh index.

Further, in step S2, a scatter diagram is drawn for fitting by using the 70% egg centroid ratio at three different temperatures as the abscissa and the egg Haugh index as the ordinate, so as to obtain the fitted equations. The rest 30% egg centroid ratio is used as a validation set to deduce the Haugh index.

Further, in step S2, a scatter diagram is drawn for fitting by using the 70% egg centroid ratio at three different placing positions as the abscissa and the egg Haugh index as the ordinate, so as to obtain the fitted equations. The rest 30% egg centroid ratio is used as a validation set to deduce the Haugh index.

Advantageous Effect

Compared with a traditional method for egg freshness detection (infrared spectroscopy, electronic nose and Haugh index measurement), the present invention has the following advantageous effects:

1. Firstly, the present invention achieves the objective of judging the egg freshness level by measuring the centroid position change of the egg in the whole storage period. The advantage is that the egg centroid is measured by the centroid measuring instrument, and the smooth implementation of non-destructive detection of egg freshness is ensured.

2. Secondly, through measurement in the whole egg period, the change trend of the egg centroid can be seen, the eggs at different shelf life can be accurately distinguished, and the method can be used for scientific research in the field of egg preservation.

3. Finally, the present invention realizes rapid measurement and low cost, and is suitable for large-scaled industrialized production. The method has the application prospects of industrial development for egg freshness detection of chicken eggs and other eggs.

DESCRIPTION OF THE EMBODIMENTS

The present invention will be illustrated in detail hereafter in conjunction with specific implementations. The embodiments provided are merely used to illustrate the present invention, and are not intended to limit the scope of the present invention.

Material and Grouping

Eggs used in this experiment were all brown healthy eggs of the same batch, totaling 420 eggs of the same batch. The surfaces of the eggs were clean without pollution, and the eggs were provided by a farm. The eggs were totally divided into 5 groups according to temperatures and big-end placing directions, including a room-temperature 25° C. big-end-up group, a 25° C. big-end-down group, a 25° C. horizontally placed group, a 4° C. horizontally placed group, and a 37° C. horizontally placed group. There were 60 eggs in each group.

Embodiment 1

(1) Sample storage: 60 eggs obtained after grouping were placed into a bought egg box in a big-end-up manner, and were stored at a 25° C. room temperature.

(2) Data acquisition: 1. Diameters of the eggs were measured by a fifty-scale vernier caliper, and data was recorded with two decimals kept.

2. The eggs were taken and placed onto a centroid measuring instrument to directly measure the distance from the centroid to the top of a small end of the egg when the egg was horizontally placed by the centroid measuring instrument and the egg mass every day, and the centroid distance was measured by respectively rotating the egg 3 times. The mean value of measured values in 3 times was taken as a final measured result. The measurement was continuously performed for 28 days (the measured Haugh index lower than 60 was used as the reference).

3. Every 4 to 5 days, 3 eggs were taken and broken to measure the albumen height, then, the egg Haugh index was calculated through a Formula $Ha=100 \times 1\ g(h+7.57-1.7 \times w^{0.37})$. In the Formula, h is the albumen height of the egg, and w is the egg mass.

(3) Data analysis: 1. Firstly, the centroid ratio was obtained by calculating the ratio of the egg centroid distance measured every day to the egg diameter.

2. Abnormal values were eliminated by using the centroid ratio of 60 eggs measured every day as a group of data through the Pauta criterion.

3. Difference significance analysis was performed on the number of days and the centroid ratio through spss software by a single-factor analysis method (see Table 1).

4. A scatter diagram was drawn for fitting by using the number of experiment days as the abscissa and the centroid ratio as the ordinate, so as to obtain relevant fitted equations.

5. A scatter diagram was drawn for fitting by using the centroid ratio as the abscissa and the Haugh index as the ordinate, so as to obtain relevant fitted equations. Then, 70% of the total egg data was used as a training set for fitting to obtain a new fitted equation. The rest 30% of egg data was used as a validation set to deduce the Haugh index. Then, the obtained Haugh index, as the practical Haugh index, was compared with the Haugh index calculated.

6. A scatter diagram was drawn by using the number of days as the abscissa and the Haugh index as the ordinate.

Embodiment 2

(1) Sample storage: 60 eggs obtained after grouping were placed into a bought egg box in a big-end-down manner, and were stored at a 25° C. room temperature.

(2) Data acquisition: The same as that in Embodiment 1.

(3) Data analysis: The same as that in Embodiment 1 (see Table 1).

Embodiment 3

(1) Sample storage: 60 eggs obtained after grouping were placed into a bought egg box in a horizontally placed manner, and were stored at a 25° C. room temperature.

(2) Data acquisition: The same as that in Embodiment 1.

(3) Data analysis: The same as that in Embodiment 1 (see Table 1).

Embodiment 4

(1) Sample storage: 60 eggs obtained after grouping were horizontally placed into a bought egg box, and were stored at 4° C.

(2) Data acquisition: 1. Diameters of the eggs were measured by a fifty-scale vernier caliper, and data was recorded with two decimals kept.

2. The eggs were taken and placed onto a centroid measuring instrument to directly measure the distance from the centroid to the top of a small end of the egg when the egg was horizontally placed by the centroid measuring instrument and the egg mass every day, and the centroid distance was measured by respectively rotating the egg 3 times. The mean value of measured values in 3 times was taken as a final measured result. The measurement was continuously performed for 39 days (the measured Haugh index lower than 60 was used as the reference).

3. Every 4 to 5 days, 3 eggs were taken and broken to measure the albumen height, then, the egg Haugh index was calculated through a Formula $Ha=100 \times 1\ g(h+7.57-1.7 \times w^{0.37})$. In the Formula, h is the albumen height of the egg, and w is the egg mass.

(3) Data analysis: 1. Firstly, the centroid ratio was obtained by calculating the ratio of the egg centroid distance measured every day to the egg diameter.

2. Abnormal values were eliminated by using the centroid ratio of 60 eggs measured every day as a group of data through the Pauta criterion.

3. Difference significance analysis was performed on the number of days and the centroid ratio through spss software by a single-factor analysis method (see Table 1).

4. A scatter diagram was drawn for fitting by using the number of experiment days as the abscissa and the centroid ratio as the ordinate, so as to obtain relevant fitted equations.

5. A scatter diagram was drawn for fitting by using the centroid ratio as the abscissa and the Haugh index as the ordinate, so as to obtain relevant fitted equations. Then, 70% of the total egg data was used as a training set for fitting to obtain a new fitted equation. The rest 30% of egg data was used as a validation set to deduce the Haugh index. Then, the obtained Haugh index, as the practical Haugh index, was compared with the Haugh index calculated.

6. A scatter diagram was drawn by using the number of days as the abscissa and the Haugh index as the ordinate.

Embodiment 5

(1) Sample storage: 60 eggs obtained after grouping were horizontally placed into a bought egg box, and were stored at 37° C.

(2) Data acquisition: 1. Diameters of the eggs were measured by a fifty-scale vernier caliper, and data was recorded with two decimals kept.

2. The eggs were taken and placed onto a centroid measuring instrument to directly measure the distance from the centroid to the top of a small end of the egg when the egg was horizontally placed by the centroid measuring instrument and the egg mass every day, and the centroid distance was measured by respectively rotating the egg 3 times. The mean value of measured values in 3 times was taken as a final measured result. The measurement was continuously performed for 26 days (the measured Haugh index lower than 60 was used as the reference).

3. Every 3 days, 3 eggs were taken and broken to measure the albumen height, then, the egg Haugh index was calculated through a Formula $Ha=100 \times 1\ g(h+7.57-1.7 \times w^{0.37})$. In the Formula, h is the albumen height of the egg, and w is the egg mass.

(3) Data analysis: 1. Firstly, the centroid ratio was obtained by calculating the ratio of the egg centroid distance measured every day to the egg diameter.

2. Abnormal values were eliminated by using the centroid ratio of 60 eggs measured every day as a group of data through the Pauta criterion.

3. Difference significance analysis was performed on the number of days and the centroid ratio through spss software by a single-factor analysis method (see Table 1).

4. A scatter diagram was drawn for fitting by using the number of experiment days as the abscissa and the centroid ratio as the ordinate, so as to obtain relevant fitted equations.

5. A scatter diagram was drawn for fitting by using the centroid ratio as the abscissa and the Haugh index as the ordinate, so as to obtain relevant fitted equations.

6. A scatter diagram was drawn by using the number of days as the abscissa and the Haugh index as the ordinate.

Comparative Example 1

(1) Sample storage: 60 eggs obtained after grouping were horizontally placed into a bought egg box, and were stored at a 25° C. room temperature.

(2) Data analysis: A relationship between the egg freshness and egg color parameters was obtained through a computer vision device and Matlab software, and was used for judging whether the egg was fresh or not. A final recognition rate on the brown shell egg freshness can reach 87%.

Comparative Example 2

(1) Sample storage: 60 eggs obtained after grouping were horizontally placed into a bought egg box, and were stored at a 25° C. room temperature.

(2) Data analysis: Transmitted hyperspectral data of the eggs was collected through a hyperspectral imager. At the same time, egg data was analyzed and processed by combining with a stoichiometric method. Models were established. A final egg freshness recognition rate can reach 88%.

Result Discussion

1. Difference significance analysis was performed on the number of days and the centroid ratio through spss software by the single-factor analysis method.

The results of the significance comparison between the measured egg centroid ratio data and the number of days are as shown in Table 1. From Table 1, it can be known that there are significance differences between the initial values of the measured egg centroid ratio of each group and the values after 10 days.

| Group | 1 d | 6 d | 11 d | 16 d | 21 d | 26 d |
|---|---|---|---|---|---|---|
| 25° C. big-end-up | 0.3972 ± 0.0326a | 0.4442 ± 0.0418b | 0.4514 ± 0.0462bc | 0.4665 ± 0.0446bc | 0.4649 ± 0.0409bc | 0.4644 ± 0.0438bc |
| 25° C. big-end-down | 0.3867 ± 0.0423a | 0.4372 ± 0.0462b | 0.4583 ± 0.0499bcd | 0.4628 ± 0.0513cd | 0.4657 ± 0.0458d | 0.4525 ± 0.0538bcd |
| 25° C. horizontally placed | 0.3878 ± 0.0381a | 0.4322 ± 0.0388b | 0.4474 ± 0.0395b | 0.4456 ± 0.0389b | 0.4555 ± 0.0462bc | 0.4548 ± 0.0443bc |
| 4° C. horizontally placed | 0.4058 ± 0.0453a | 0.4165 ± 0.0504a | 0.4545 ± 0.0412b | 0.4517 ± 0.0395b | 0.4549 ± 0.0394b | 0.4521 ± 0.0413b |
| 37° C. horizontally placed | 0.4152 ± 0.0445a | 0.4452 ± 0.0344b | 0.4175 ± 0.0425c | 0.4861 ± 0.0422c | 0.4908 ± 0.0383c | 0.4726 ± 0.0425c |

2. A scatter diagram was drawn for fitting by using the number of experiment days as the abscissa and the centroid ratio as the ordinate, and a fitting diagram was drawn.

Figure 1:
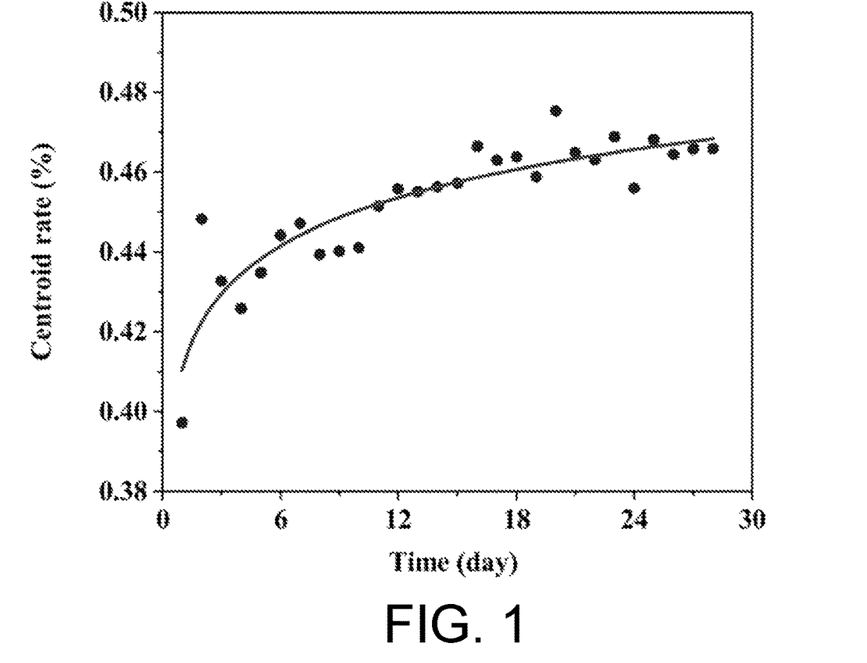
FIG. 1 is a scatter diagram between the egg centroid ratio at a big-end-up position and the number of days at 25° C.
Figure 2:
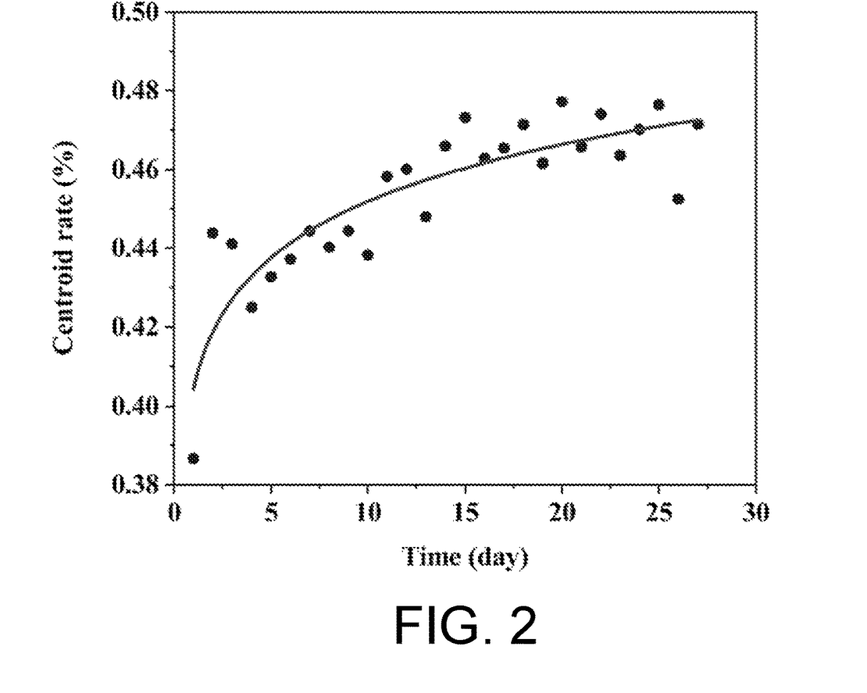
FIG. 2 is a scatter diagram between the egg centroid ratio at a big-end-down position and the number of days at 25° C.
Figure 3:
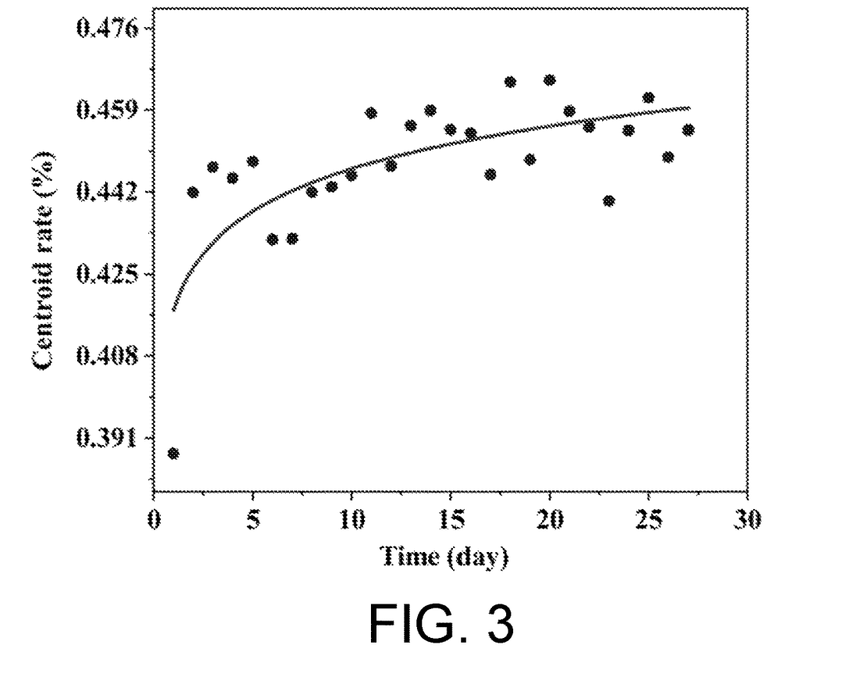
FIG. 3 is a scatter diagram between the egg centroid ratio at a horizontally placed position and the number of days at 25° C.
Figure 4:
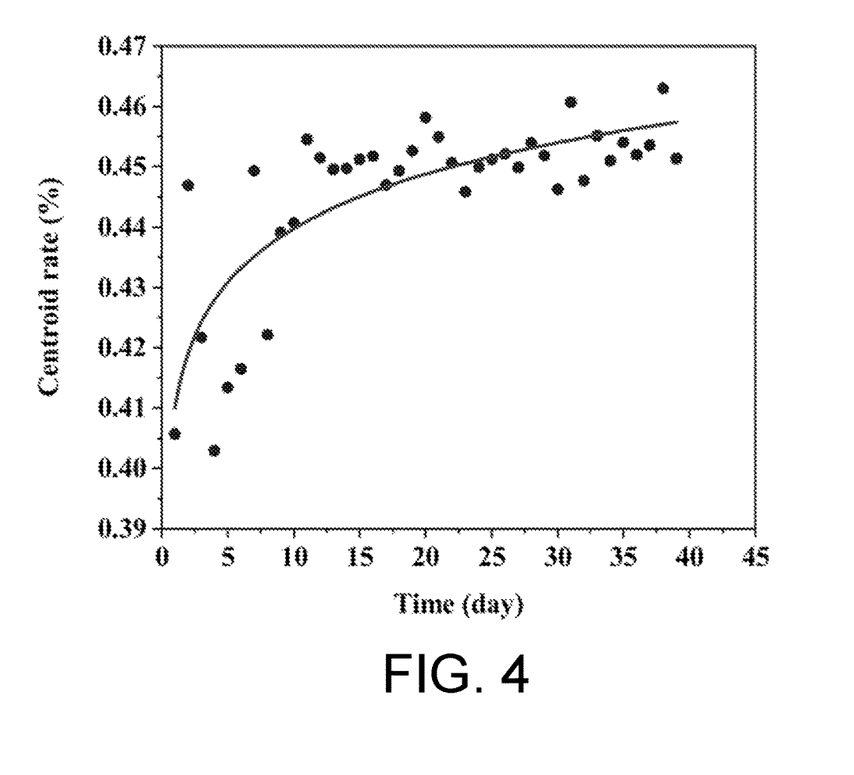
FIG. 4 is a scatter diagram between the egg centroid ratio at a horizontally placed position and the number of days at 4° C.
Figure 5:
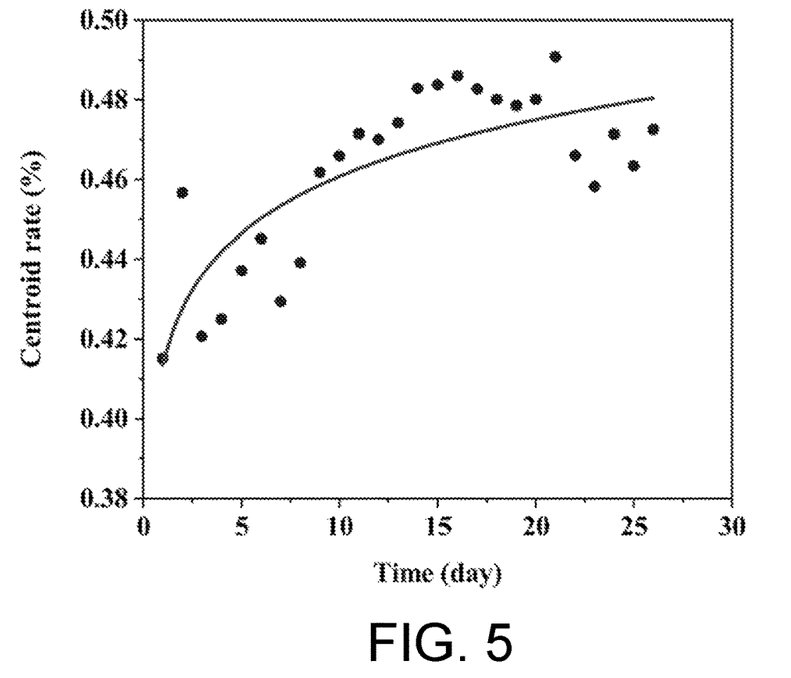
FIG. 5 is a scatter diagram between the egg centroid ratio at a horizontally placed position and the number of days at 37° C.

In Embodiments 1-5, a scatter diagram was drawn for fitting and drawing by using the number of experiment days as the abscissa and the centroid ratio as the ordinate. With reference to FIGS. 1-5, it could be known from the figures that for the 25° C. big-end-up and big-end-down groups of the eggs, determination coefficients of fitted logarithmic equations can reach 0.75 or higher, and the fitting degree is higher, which proves that the egg freshness measurement through the centroid is feasible.

3. A scatter diagram was drawn for fitting by using the centroid ratio as the abscissa and the Haugh index as the ordinate, and a fitting diagram was drawn.

Figure 6:
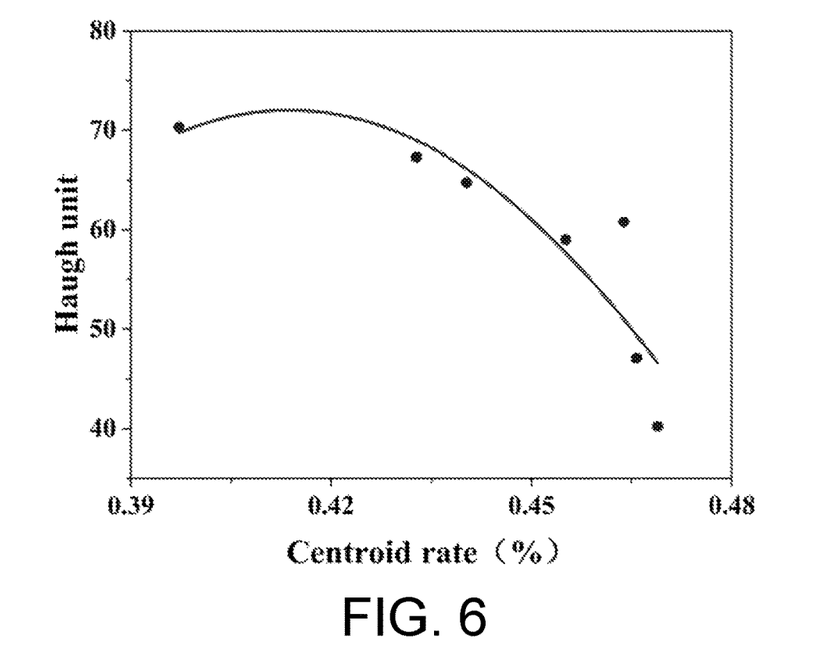
FIG. 6 is a scatter diagram between the egg centroid ratio at a big-end-up position and the Haugh index at 25° C.
Figure 7:
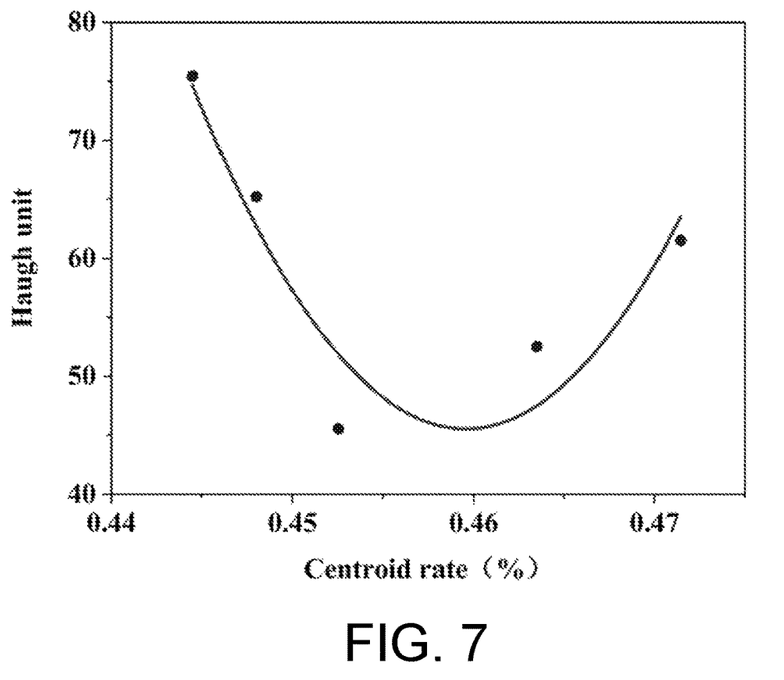
FIG. 7 is a scatter diagram between the egg centroid ratio at a big-end-down position and the Haugh index at 25° C.
Figure 8:
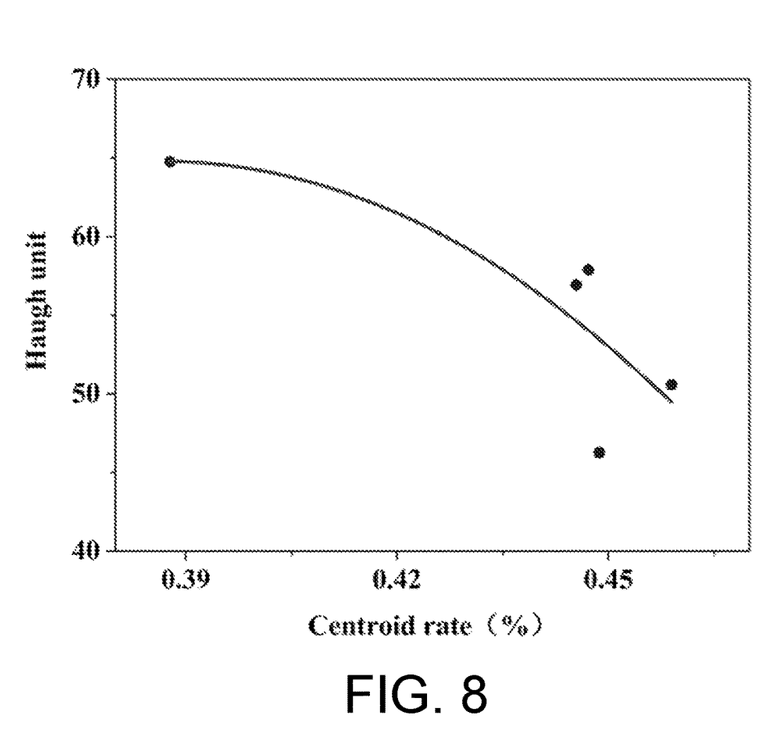
FIG. 8 is a scatter diagram between the egg centroid ratio at a horizontally placed position and the Haugh index at 25° C.
Figure 9:
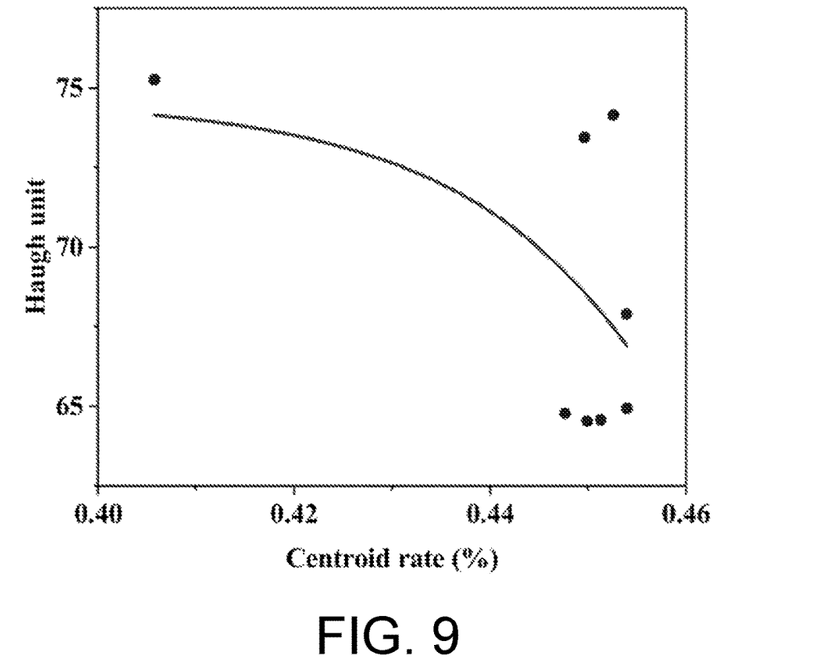
FIG. 9 is a scatter diagram between the egg centroid ratio at a horizontally placed position and the Haugh index at 4° C.

Quadratic equation fitting was performed between the egg centroid ratio and the egg Haugh index of the practical corresponding number of days in Embodiments 1-5. With reference to FIGS. 6-9, it can be known from the figures that for the 25° C. big-end-up and big-end-down groups, determination coefficients of fitted equations can all reach 0.79 or higher, and the fitting degree is higher. For Embodiment 5, the eggs were stored at 37° C. The measured egg Haugh index was 60 or below, and was lower than the edible egg standard grade, so this condition was not discussed in this study.

4. A scatter diagram was drawn for fitting by using 70% of total egg data and using the centroid ratio as the abscissa and the Haugh index as the ordinate, a fitting diagram was drawn, and the rest 30% of egg data was used as a validation set to deduce the Haugh index.

Figure 10:
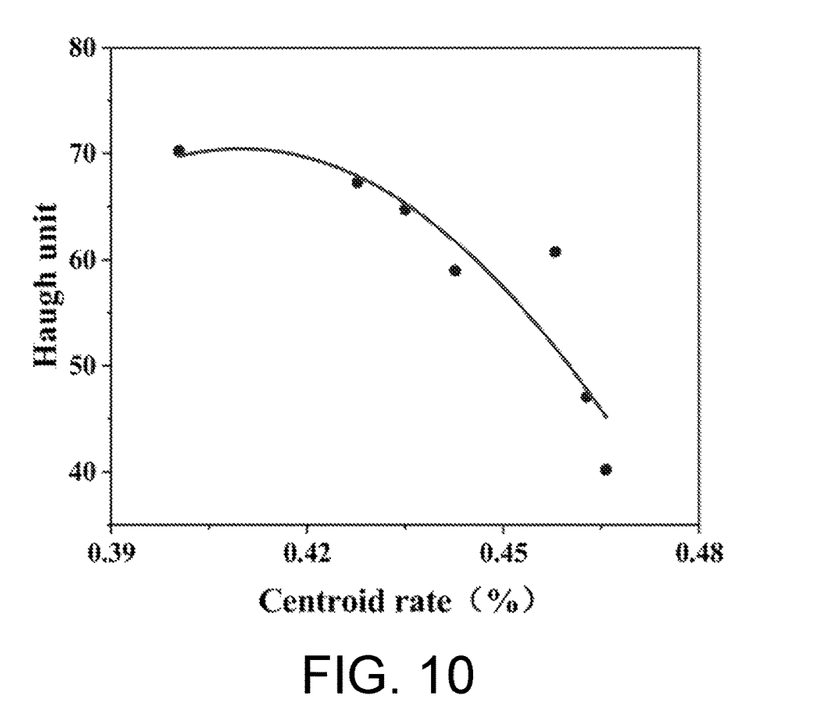
FIG. 10 is a scatter diagram between the 70% egg centroid ratio at a big-end-up position as a training set and the Haugh index at 25° C.
Figure 11:
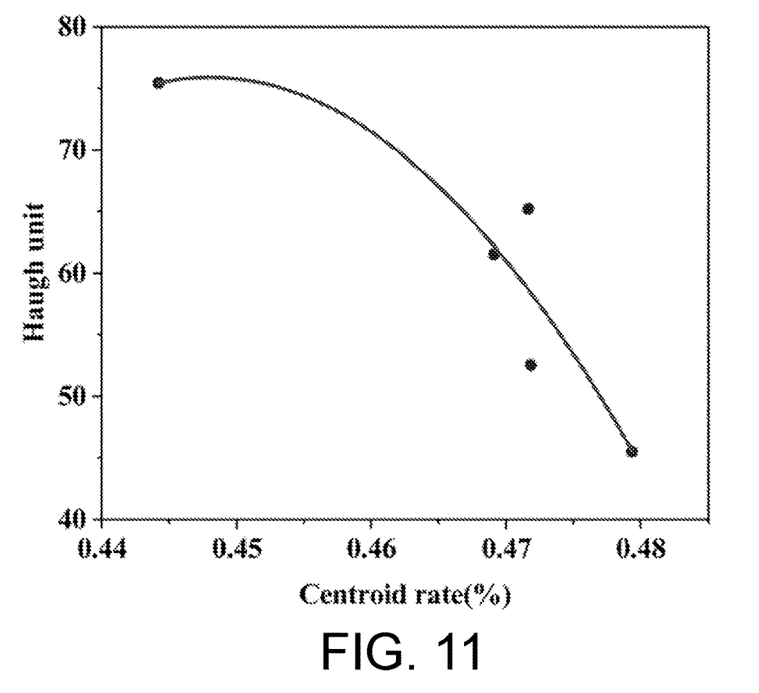
FIG. 11 is a scatter diagram between the 70% egg centroid ratio at a big-end-down position as a training set and the Haugh index at 25° C.
Figure 12:
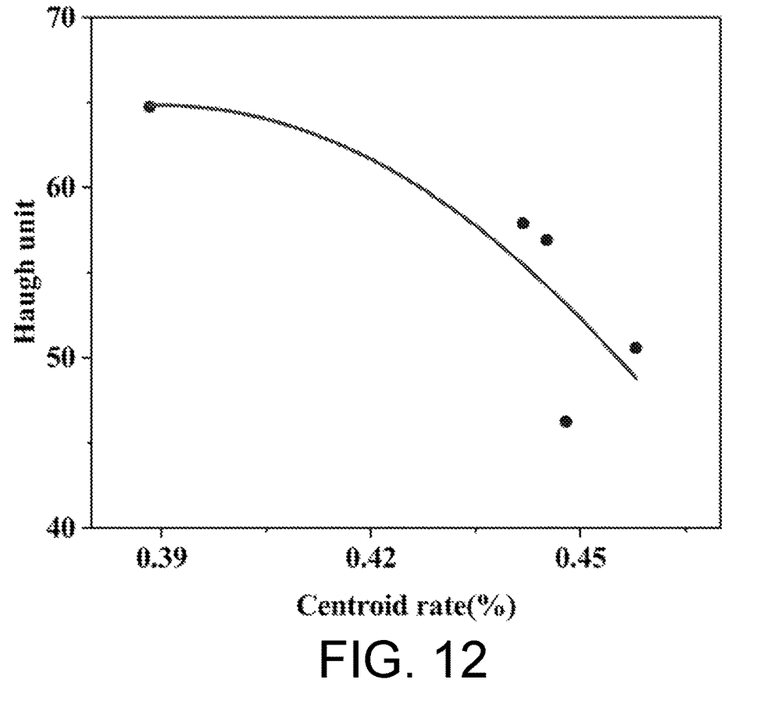
FIG. 12 is a scatter diagram between the 70% egg centroid ratio at a horizontally placed position as a training set and the Haugh index at 25° C.
Figure 13:
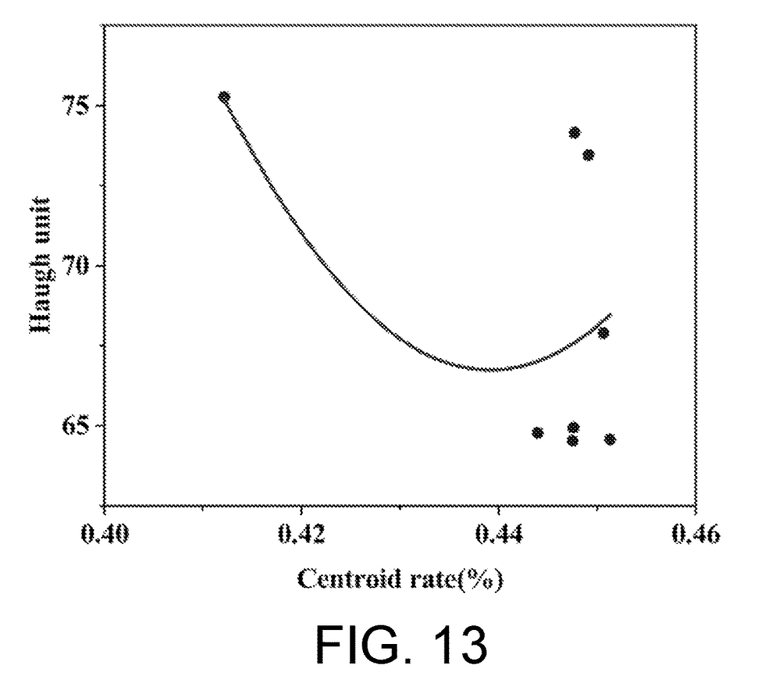
FIG. 13 is a scatter diagram between the 70% egg centroid ratio at a horizontally placed position as a training set and the Haugh index at 4° C.

70% of the data of the egg centroid ratio measured in Embodiments 1-4 and the Haugh index of the corresponding number of days were subjected to equation fitting. With reference to FIGS. 10-13, it is found that for the 25° C. big-end-up and big-end-down groups, determination coefficients of training set fitted equations were all between 0.84 and 0.85, and the fitting degree is higher.

According to the fitted training set equations, Embodiment 1 was validated. The rest 30% of validation set data was respectively substituted into the equations to deduce the Haugh index of the corresponding number of days, and the Haugh index was compared with the practically measured Haugh index through paired T test. The results are as shown in Table 2 below.

| | | Paired sample test | | | | | | | |
|---|---|---|---|---|---|---|---|---|---|
| | | Paired difference | | | | | | | |
| | | Mean value | Standard deviation | Standard error of mean value | 99% confidence interval of difference | | t | df | Sig. (two-sided) |
| | | | | | Lower limit | Upper limit | | | |
| Pair 1 | Haugh index-validation set 1 | −9.00714 | 14.80492 | 5.59574 | −29.75293 | 11.73864 | −1.610 | 6 | 0.159 |
| Pair 2 | Haugh index-validation set 2 | 7.62571 | 5.21029 | 1.96930 | 0.32466 | 14.92677 | 3.872 | 6 | 0.008 |
| Pair 3 | Haugh index-validation set 3 | −6.71286 | 18.14720 | 6.85900 | −32.14209 | 18.71638 | −0.979 | 6 | 0.366 |
| Pair 4 | Haugh index-validation set 4 | 5.41714 | 6.56602 | 2.48172 | −3.78366 | 14.61795 | 2.183 | 6 | 0.072 |
| Pair 5 | Haugh index-validation set 5 | 24.29571 | 17.58601 | 6.64689 | −0.34714 | 48.93856 | 3.655 | 6 | 0.011 |
| Pair 6 | Haugh index-validation set 6 | 27.86429 | 26.82594 | 10.13925 | −9.72626 | 65.45483 | 2.748 | 6 | 0.033 |
| Pair 7 | Haugh index-validation set 7 | 96.72143 | 46.78132 | 17.68168 | 31.16789 | 162.27497 | 5.470 | 6 | 0.002 |

-continued

| | | Paired sample test | | | | | | | |
|---|---|---|---|---|---|---|---|---|---|
| | | Paired difference | | | | | | | |
| | | Mean value | Standard deviation | Standard error of mean value | 99% confidence interval of difference | | t | df | Sig. (two-sided) |
| | | | | | Lower limit | Upper limit | | | |
| Pair 8 | Haugh index-validation set 8 | −3.16857 | 25.33265 | 9.57484 | −38.66661 | 32.32946 | −0.331 | 6 | 0.752 |

Results in Table 2 show that the paired sample T test result is between −1.61 and 5.47. Two groups have the validation set difference significance level P>0.01. It shows that the Haugh indexes predicted by these two groups have very significant differences from the practical Haugh index. The results of the other six groups of validation sets show that there was no significant difference from the practical Haugh index at the level of $\alpha=0.01$. Based on the above, the results show that the present invention can reach a 75% correctness rate on the freshness prediction of eggs stored at 25° C. in a big-end-up manner.

According to the fitted training set equations, Embodiment 2 was validated. The rest 30% of validation set data was respectively substituted into the equations to reduce the Haugh index of the corresponding number of days, and the Haugh index was compared with the practically measured Haugh index through paired T test. The results are as shown in Table 3 below.

| | | Paired sample test | | | | | | | |
|---|---|---|---|---|---|---|---|---|---|
| | | Paired difference | | | | | | | |
| | | Mean value | Standard deviation | Standard error of mean value | 99% confidence interval of difference | | t | df | Sig. (two-sided) |
| | | | | | Lower limit | Upper limit | | | |
| Pair 1 | Haugh index-validation set 1 | 62.11650 | 63.89544 | 31.94772 | −124.48722 | 248.72023 | 1.944 | 3 | 0.147 |
| Pair 2 | Haugh index-validation set 2 | 2.50089 | 7.24185 | 3.62093 | −18.64862 | 23.65039 | 0.691 | 3 | 0.539 |
| Pair 3 | Haugh index-validation set 3 | 73.41614 | 79.18707 | 39.59354 | −157.84613 | 304.67840 | 1.854 | 3 | 0.161 |
| Pair 4 | Haugh index-validation set 4 | 78.32911 | 46.65337 | 23.32669 | −57.91995 | 214.57817 | 3.358 | 3 | 0.044 |
| Pair 5 | Haugh index-validation set 5 | 57.78312 | 23.62112 | 13.63766 | −77.56850 | 193.13473 | 4.237 | 2 | 0.051 |
| Pair 6 | Haugh index-validation set 6 | 97.82722 | 127.4453 | 56.99529 | −164.58450 | 360.23895 | 1.716 | 4 | 0.161 |
| Pair 7 | Haugh index-validation set 7 | 38.15735 | 53.86537 | 24.08933 | −72.75219 | 149.06689 | 1.584 | 4 | 0.188 |
| Pair 8 | Haugh index-validation set 8 | 35.81883 | 80.67941 | 40.33970 | −199.80172 | 271.43939 | 0.888 | 3 | 0.440 |
| Pair 9 | Haugh index-validation set 9 | 23.55192 | 48.17367 | 34.06393 | −2144.8469 | 2191.9508 | 0.691 | 1 | 0.615 |
| Pair 10 | Haugh index-validation set 10 | 80.89393 | 40.64079 | 28.73738 | −1748.4338 | 1910.2217 | 2.815 | 1 | 0.217 |
| Pair 11 | Haugh index-validation set 11 | 123.0774 | 181.4436 | 128.30000 | −8044.0827 | 8290.2376 | 0.959 | 1 | 0.513 |
| Pair 12 | Haugh index-validation set 12 | 65.38667 | 8.19189 | 4.72959 | 18.44624 | 112.32709 | 13.825 | 2 | 0.005 |

Results in Table 3 show that the paired sample T test result is between 0.691 and 13.825. Only one group has the validation set difference significance level P>0.01. It shows that the Haugh index predicted by this group has very significant differences from the practical Haugh index. The results of the other eleven groups of validation sets show that there is no significant difference from the practical Haugh index at the level of α=0.01. Based on the above, the results show that the present invention can reach a 91.6% correctness rate on the freshness prediction of eggs stored at 25° C. in a big-end-down manner.

Figure 14:
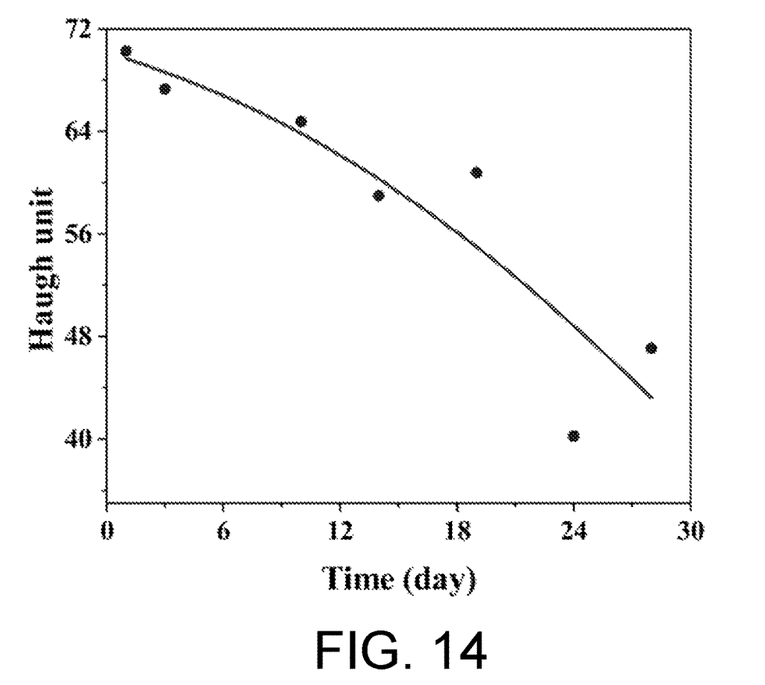
FIG. 14 is a scatter diagram of the egg Haugh index measured at a big-end-up position and the number of days at 25° C.
Figure 15:
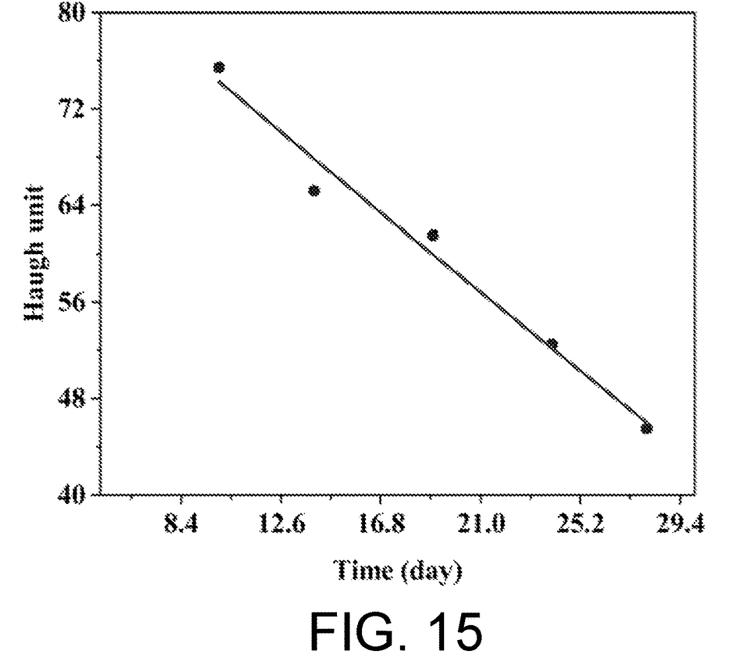
FIG. 15 is a scatter diagram of the egg Haugh index measured at a big-end-down position and the number of days at 25° C.
Figure 16:
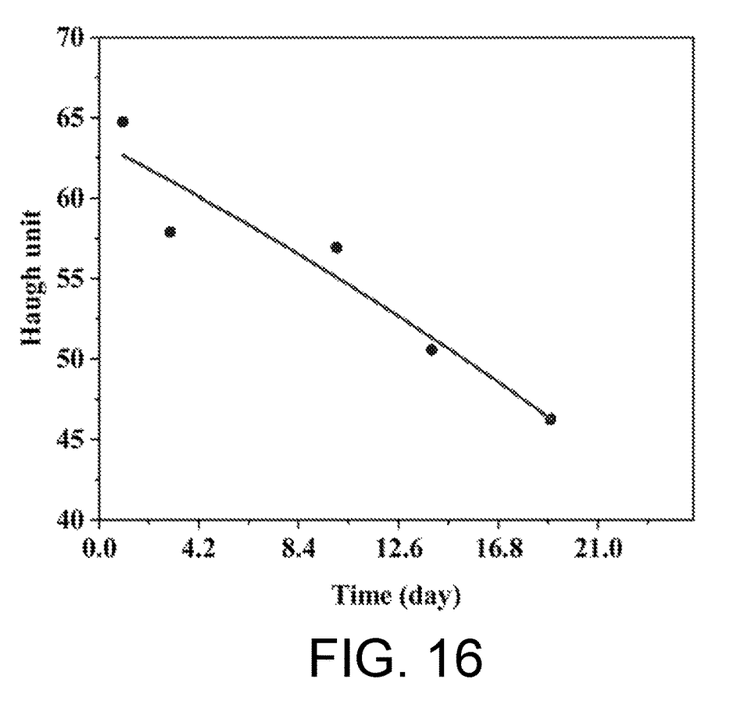
FIG. 16 is a scatter diagram of the egg Haugh index measured at a horizontally placed position and the number of days at 25° C.
Figure 17:
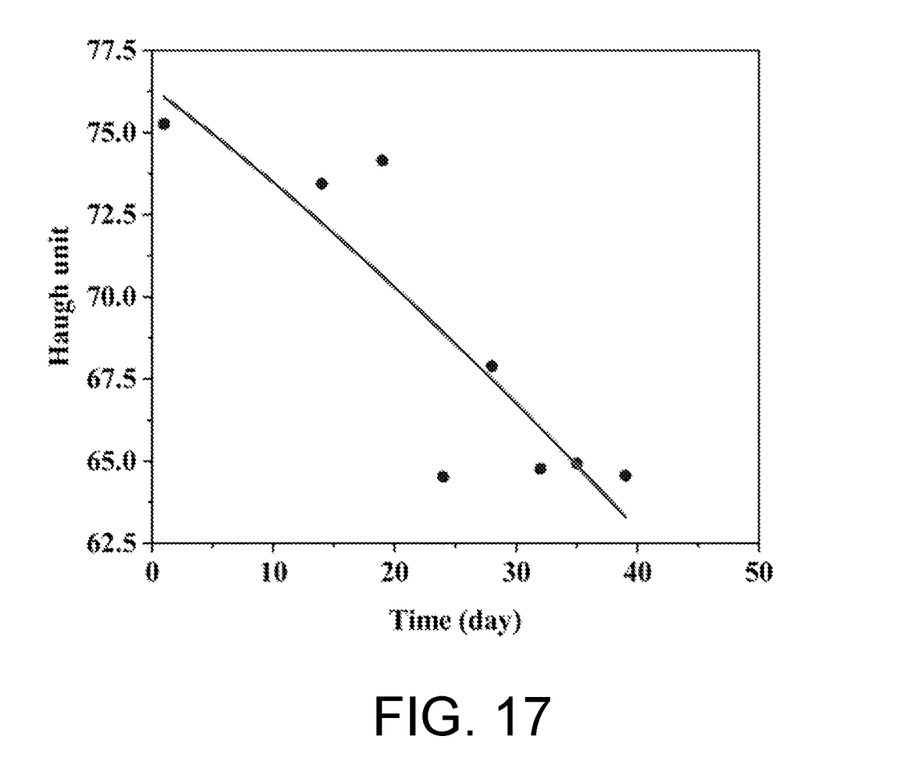
FIG. 17 is a scatter diagram of the egg Haugh index measured at a horizontally placed position and the number of days at 4° C.

5. Relevant fitted equations of eggs at different temperatures and different placing positions With reference to FIGS. 14-17, a scatter diagram of the number of days and the Haugh index was obtained. The relevant fitted equations of eggs at different temperatures and different placing positions are shown in Table 4 below.

| Group | Fitting of centroid and number of days | R2 | Fitting of centroid and Haugh index | R2 |
|---|---|---|---|---|
| 25° C. big-end-up | y = 0.01741n(x) + 0.4104 | 0.790 | y = −8371.5x2 + 6927.1x − 1361 | 0.796 |
|  |  |  | Training set: y = −8076.1x2 + 6619.6x − 1286 | 0.841 |
| 25° C. big-end-down | y = 0.02071n(x) + 0.4043 | 0.758 | y = 127986x2 − 117640x + 27078 | 0.857 |
|  |  |  | Training set: y = −30913x2 + 27701x − 6129.7 | 0.854 |
| 25° C. horizontally placed | y = 0.01281n(x) + 0.4174 | 0.525 | y = −2889.4x2 + 2231.4x − 366.01 | 0.637 |
|  |  |  | Training set: y = −3437.1x2 + 2678x − 456.81 | 0.687 |
| 4° C. big-end-up | y = 0.01291n(x) + 0.4100 | 0.594 | y = 7689.8x2 − 6756x + 1550.5 | 0.314 |
|  |  |  | Training set: y = 11636x2 − 10220x + 2310.9 | 0.312 |
| 37° C. horizontally placed | y = 0.02061n(x) + 0.4134 | 0.619 |  |  |

The centroid changes of the eggs in different periods were measured and were compared by using a computer vision device and a hyperspectral imaging technology. The results show that the finial recognition rate of the egg freshness by the egg centroid ratio measurement method can up to 91.6%, which is higher than the recognition rate of the comparative example. Compared with the measurement method involved in the present invention, the hyperspectral imaging technology or the computer vision device has the lower recognition rate than the present invention, and has the defects of high cost and measurement complexity. The present invention has the advantages of simple measurement, low cost, high speed and high recognition rate. The egg grades can be distinguished in real time by measuring the centroid changes of the eggs in the whole period. This is also the innovation of egg freshness detection based on centroid measurement of the present invention.

What is claimed is:

1. A method for non-destructive detection of egg freshness based on centroid measurement, comprising the following steps:
   S1, data acquisition: accurately measuring a centroid position of an egg by a centroid measuring instrument, and obtaining a value of an egg centroid ratio by calculating a ratio of a distance from the centroid position to a top of a small end of the egg to a length of the egg; and
   S2, data processing: establishing mathematical models between the egg centroid ratio at different temperatures and different placing positions and an egg Haugh index, wherein according to the established models, the egg freshness is able to be directly represented according to the centroid ratio, and an objective of rapid, accurate, and non-destructive detection of the egg freshness is achieved.

2. The method for non-destructive detection of egg freshness based on centroid measurement according to claim 1, wherein in step S2, fitted equations are respectively established between the egg centroid ratio at three different temperatures and a number of days the egg has been stored.

3. The method for non-destructive detection of egg freshness based on centroid measurement according to claim 1, wherein in step S2, fitted equations are respectively established between the egg centroid ratio at three different placing positions and a number of days the egg has been stored.

4. The method for non-destructive detection of egg freshness based on centroid measurement according to claim 1, wherein in step S2, fitted equations are respectively established between the egg centroid ratio at three different temperatures and the egg Haugh index.

5. The method for non-destructive detection of egg freshness based on centroid measurement according to claim 1, wherein in step S2, fitted equations are respectively established between the egg centroid ratio at three different placing positions and the egg Haugh index.

6. The method for non-destructive detection of egg freshness based on centroid measurement according to claim 1, wherein in step S2, a scatter diagram is drawn for fitting by using the 70% egg centroid ratio at three different temperatures as an abscissa and the egg Haugh index as an ordinate, so as to obtain fitted equations, and the rest 30% egg centroid ratio is used as a validation set to deduce the egg Haugh index.

7. The method for non-destructive detection of egg freshness based on centroid measurement according to claim 1, wherein in step S2, a scatter diagram is drawn for fitting by using the 70% egg centroid ratio at three different placing positions as an abscissa and the egg Haugh index as an ordinate, so as to obtain fitted equations, and the rest 30% egg centroid ratio is used as a validation set to deduce the egg Haugh index.

* * * * *